US012611273B2

(12) United States Patent
Wixey et al.

(10) Patent No.: US 12,611,273 B2
(45) Date of Patent: Apr. 28, 2026

(54) SURGICAL INSTRUMENT STEERING INPUT DEVICE

(71) Applicant: INTUITIVE SURGICAL OPERATIONS, INC., Sunnyvale, CA (US)

(72) Inventors: Matthew Aaron Wixey, Trumbull, CT (US); Nicholas H. Ragosta, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 134 days.

(21) Appl. No.: 18/540,205

(22) Filed: Dec. 14, 2023

(65) Prior Publication Data

US 2024/0189054 A1    Jun. 13, 2024

Related U.S. Application Data

(63) Continuation of application No. 17/063,048, filed on Oct. 5, 2020, now Pat. No. 11,877,819, which is a (Continued)

(51) Int. Cl.
*A61B 34/00* (2016.01)
*A61B 17/00* (2006.01)
(Continued)

(52) U.S. Cl.
CPC ........ *A61B 34/71* (2016.02); *A61B 17/00234* (2013.01); *A61B 34/35* (2016.02);
(Continued)

(58) Field of Classification Search
CPC ... A61B 34/71; A61B 34/35; A61B 17/00234; A61B 17/1631; A61B 2017/00477;
(Continued)

(56) References Cited

U.S. PATENT DOCUMENTS 10,792,115 B2    10/2020    Wixey et al.
2008/0009838 A1*    1/2008    Schena .................. A61B 34/37
606/1

(Continued)

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Brooke Labranche
(74) *Attorney, Agent, or Firm* — Jones Burke, PLLC

(57) ABSTRACT

A drive assembly of an instrument includes an input drive interface removably engageable with an external actuator device and configured to receive drive actuation force from the external actuator device in a state of engagement with the external actuator device, a drive shaft configured to be driven in rotation, a capstan, and a splined snap-fit connection mechanism between the drive shaft and the capstan. The splined snap-fit connection mechanism includes splined engagement features configured to engage each other so as to prevent relative rotation between the drive shaft and the capstan, and a plurality of snap-fit elements to provide a snap-fit engagement between the drive shaft and the capstan so as to provide resistance to relative axial movement between the drive shaft and the capstan.

20 Claims, 7 Drawing Sheets

Related U.S. Application Data continuation of application No. 15/782,449, filed on Oct. 12, 2017, now Pat. No. 10,792,115.

(60) Provisional application No. 62/408,348, filed on Oct. 14, 2016.

(51) Int. Cl.
  *A61B 34/35*          (2016.01)
  *A61B 17/16*          (2006.01)
  *A61B 17/29*          (2006.01)
  *A61B 34/30*          (2016.01)

(52) U.S. Cl.
  CPC .  *A61B 2017/00477* (2013.01); *A61B 17/1631* (2013.01); *A61B 2017/2901* (2013.01); *A61B 2034/301* (2016.02); *A61B 2034/305* (2016.02)

(58) Field of Classification Search
  CPC ...... A61B 2017/2091; A61B 2034/301; A61B 2034/305
  See application file for complete search history.

(56)          References Cited

U.S. PATENT DOCUMENTS

| | | |
|---|---|---|
| 2010/0170519 A1 | 7/2010 | Romo et al. |
| 2013/0331857 A9 | 12/2013 | Prisco et al. |
| 2015/0051034 A1 | 2/2015 | Cooper et al. |
| 2015/0148829 A1 | 5/2015 | Kimball et al. |
| 2021/0059778 A1 | 3/2021 | Wixey et al. |

* cited by examiner

SURGICAL INSTRUMENT STEERING INPUT DEVICE

CROSS REFERENCE TO RELATED APPLICATIONS

This application is a continuation of U.S. patent application Ser. No. 17/063,048, filed Oct. 5, 2020, which is a continuation of Ser. No. 15/782,449, filed Oct. 12, 2017 (now U.S. Pat. No. 10,792,115), which claims the benefit of U.S. Provisional Application No. 62/408,348, filed Oct. 14, 2016, each of which is hereby incorporated by reference in their entirety.

TECHNICAL FIELD

This specification generally relates to surgical instruments for use with teleoperated robotic systems. In particular, the present disclosure describes steering input devices incorporated in such surgical instruments.

BACKGROUND

Minimally invasive medical techniques (e.g., laparoscopy) have been used to reduce the amount of extraneous tissue which may be damaged during diagnostic or surgical procedures, thereby reducing patient recovery time, discomfort, and deleterious side effects. Such techniques were traditionally performed manually via a surgeon manipulating various surgical instruments within the patient's body, but can now by implemented using teleoperated robotic systems that provide telepresence. Performing minimally invasive surgery with teleoperated robotic systems facilitates increased precision and range of motion in manipulating surgical instruments when compared to manual techniques, but also introduces new challenges. One such challenge is the need to manufacture, assemble, and tune (or "pre-tension") surgical instruments. Pre-tensioning tension actuation elements, such as cables or cable-hypotube combinations, enables the instruments' end effectors at the surgical site to respond rapidly and accurately to remote actuating signals. Conventional mechanically actuated surgical instruments include steering input devices that are expensive to produce because they include multiple intricate components that must be machined to precise tolerances. Further, their complicated assembly makes multi-step pretensioning procedures cumbersome and difficult to automate.

SUMMARY

One aspect of the present disclosure features a surgical instrument including: an adjustable end effector; an elongated instrument shaft defining an internal bore and extending from a first end coupled to the end effector to a second end; and a drive assembly including a housing coupled to the second end of the instrument shaft and an input device configured to facilitate controlled adjustment of the end effector via a drive cable extending along the bore of the instrument shaft. The input device includes a drive shaft and a capstan attached to first and second portions, respectively, of the drive cable. The capstan defines an internal bore with a plurality of vertical splines projecting inwardly to engage an outer surface of the drive shaft, such that when the splines engage the outer surface, relative rotation between the drive shaft and the capstan is inhibited as the end effector is adjusted.

In some examples, the outer surface of the drive shaft includes a plurality of diametrically-spaced vertical splines projecting outwardly between the inwardly projecting splines of the capstan, such that the engagement between the drive shaft and capstan includes a keyed mesh of splines. In some examples, each of the vertical splines of the drive shaft and/or the capstan include a lead-in surface angled from the vertical direction.

In some examples, the drive shaft and the capstan each include a coupling facilitating attachment to the respective first and second portions of the cable. In some examples, the coupling of the drive shaft and/or the capstan includes an outwardly facing helical groove. In some examples, the coupling further includes an outwardly facing spool. In some examples, the coupling further includes a tortuous path including two or more sharp bends.

In some examples, the drive shaft further includes a snap-fit element configured to engage an undercut ridge formed along the internal bore of the capstan, such that when the snap-fit element engages the undercut ridge of the capstan, relative vertical movement between the drive shaft and the capstan is resisted. Similarly, in some examples the snap-fit element engages a groove formed along the internal bore of the capstan. In some examples, the snap-fit element includes a plurality of diametrically-spaced snap fingers, with each of the snap fingers including a vertical stem and a lip projecting radially outward from an upper end of the stem. In some examples, the snap-fit element includes a beveled upper edge to facilitate sliding contact with the undercut ridge as the capstan is lowered relative to the drive shaft. In some examples, the snap-fit element further includes a beveled lower edge to facilitate sliding contact with the undercut ridge or groove as the capstan is raised relative to the drive shaft.

Another aspect of the present disclosure features a method of tensioning a cable of a drive assembly for a surgical instrument including the steps of: coupling respective portions of the cable to a drive shaft of the drive assembly and to a capstan of the drive assembly; and then independently rotating the drive shaft and the capstan to tension the cable; and after tensioning the cable, securing the capstan to the drive shaft by engaging a plurality of internal splines of the capstan with an outer surface of the drive shaft, such that relative rotation between the drive shaft and the capstan is inhibited by the engaged splines.

In some examples, engaging the plurality of internal splines of the capstan includes meshing the internal splines with a plurality of outwardly projecting diametrically-spaced vertical splines of the drive shaft. In some examples, securing the capstan to the drive shaft further includes engaging a snap-fit element of the drive shaft with an undercut ridge formed along an internal bore of the capstan, such that relative vertical movement between the drive shaft and the capstan is resisted. In some examples, securing the capstan to the drive shaft includes the steps of: placing the capstan above the drive shaft; and pressing the capstan down over the drive shaft to simultaneously engage the internal splines of the capstan and the snap-fit element of the drive shaft.

In some examples, coupling the respective portions of the cable to the drive shaft and capstan includes routing one of the cable portions along an outwardly facing helical groove. In some examples, coupling the respective portions of the cable to the drive shaft and capstan further includes wrapping one of the cable portions around itself in an outwardly facing spool. In some examples, coupling the respective portions of the cable to the drive shaft and capstan further includes routing one of the cable portions through two or more bends of a tortuous path.

In some examples, independently rotating the drive shaft and the capstan includes alternately fixing one of the drive shaft and capstan in place while rotating the other.

In some examples, independently rotating the drive shaft and the capstan includes simultaneously rotating the drive shaft and capstan in opposite angular directions.

In some examples, the method further includes the steps of: disengaging the splines of the capstan from the outer surface of the drive shaft; further tensioning the cable to a predetermined set point by independently rotating the drive shaft and the capstan; and after further tensioning the cable, re-engaging the splines of the capstan with the outer surface of the drive shaft to secure the capstan in place.

Yet another aspect of the present disclosure features a surgical instrument including: a distal movable component; a proximal drive assembly including a drive shaft, a capstan, and a plurality of splines; a first cable extending between the distal movable component and the drive shaft; and a second cable extending between the distal movable component and the capstan. The drive shaft includes a tapered projection, and the capstan includes a tapered bore in which the tapered projection of the drive shaft is received. The plurality of splines engage the tapered projection of the drive shaft with the tapered bore of the capstan.

In some examples, the drive shaft includes a snap-fit element engaged with the capstan.

In some examples, the drive shaft includes a snap-fit element engaged with the capstan; the snap-fit element includes an elastic portion and a lip on the elastic portion; and the lip of the snap-fit element is beveled to facilitate engagement with the capstan, disengagement from the capstan, or both engagement with and disengagement from the capstan.

In some examples, the tapered bore of the capstan includes the plurality of splines; the tapered projection of the drive shaft includes a conical surface; and the plurality of splines engage the conical surface of the drive shaft. In some examples, the drive shaft includes a snap-fit element engaged with the capstan. In some examples, the drive shaft includes a snap-fit element engaged with the capstan; the snap-fit element includes an elastic portion and a lip on the elastic portion; and the lip of the snap-fit element is beveled to facilitate engagement with the capstan, disengagement from the capstan, or both engagement with and disengagement from the capstan.

In some examples, the tapered projection of the drive shaft includes the plurality of splines; the tapered bore of the capstan includes a conical surface; and the plurality of splines engage the conical surface of the capstan. In some examples, the drive shaft includes a snap-fit element engaged with the capstan. In some examples, the drive shaft includes a snap-fit element engaged with the capstan; the snap-fit element includes an elastic portion and a lip on the elastic portion; and the lip of the snap-fit element is beveled to facilitate engagement with the capstan, disengagement from the capstan, or both engagement with and disengagement from the capstan.

In some examples, the tapered projection of the drive shaft includes a first portion of the plurality of splines; the tapered bore of the capstan includes a second portion of the plurality of splines; and the first and second portions of the plurality of splines are meshed. In some examples, the drive shaft includes a snap-fit element engaged with the capstan. In some examples, the drive shaft includes a snap-fit element engaged with the capstan; the snap-fit element includes an elastic portion and a lip on the elastic portion; and the lip of the snap-fit element is beveled to facilitate engagement with the capstan, disengagement from the capstan, or both engagement with and disengagement from the capstan.

In some examples, the tapered projection of the drive shaft includes a first portion of the plurality of splines, and upper edges of the first portion of splines are chamfered; the tapered bore of the capstan includes a second portion of the plurality of splines, and lower edges of the second portion of the plurality of splines are chamfered; and the first and second portions of the plurality of splines are meshed. In some examples, the drive shaft includes a snap-fit element engaged with the capstan. In some examples, the drive shaft includes a snap-fit element engaged with the capstan; the snap-fit element includes an elastic portion and a lip on the elastic portion; and the lip of the snap-fit element is beveled to facilitate engagement with the capstan, disengagement from the capstan, or both engagement with and disengagement from the capstan.

Yet another aspect of the present disclosure features a method of making a surgical instrument including the steps of: coupling a first cable between a drive shaft and a distal movable component; coupling a second cable between a capstan and the distal movable component; and coupling the drive shaft and the capstan by engaging a plurality of splines between the drive shaft and the capstan.

In some examples, the method further includes the steps of: rotating the drive to place a first desired tension on the first cable; rotating the capstan to place a second desired tension on the second cable; and coupling the drive shaft and the capstan while maintaining the first and second desired tensions.

In some examples, engaging a plurality of splines between the drive shaft and the capstan includes meshing a first portion of the plurality of splines on the drive shaft with a second portion of the plurality of splines on the capstan.

In some examples, coupling the drive shaft and the capstan includes engaging a snap-fitting between the drive shaft and the capstan.

Yet another aspect of the present disclosure features a method of disassembling a surgical instrument including the steps of: disengaging a plurality of splines on a tapered surface of a capstan from a plurality of splines on a tapered surface of a drive shaft; and disengaging a snap-fitting between the capstan and the drive shaft.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

One or more of the illustrated elements may be exaggerated to better show the features, process steps, and results. Like reference numbers and designations in the various drawings may indicate like elements.

DETAILED DESCRIPTION

Various embodiments of the present disclosure relate to surgical instruments for use with teleoperated robotic systems. More specifically, embodiments include a drive assembly for the surgical instruments featuring a steering input device that is easier to manufacture, assemble, and tune than in prior systems. For example, the input devices described herein include multiple components that can be manufactured by molding instead of machining. Further, certain embodiments provide drive assemblies that include a quick engage-release coupling that can be assembled (and disassembled) without special tools or fasteners. This simplifies the tuning (e.g., drive cable pre-tensioning) process, which enables such processes to be automated.

Minimally invasive surgery can be performed by inserting surgical instruments through orifices in a patient's body (e.g., natural orifices or body-wall incisions) and controlling the surgical instruments via an interface on the outside of the body. In various embodiments of the present disclosure, the surgical instruments are teleoperated by surgeons. Thus, the surgeons do not move the instruments by direct physical contact, but instead control instrument motion from some distance away by moving master input devices ("masters"). The operating surgeon is typically provided with a view of the actual surgical site via a visual display, so that the surgeon may remotely perform surgical motions with the masters while viewing the surgical site. A controller of the surgical system causes the surgical instrument to be moved in accordance with movement of a master.

Figure 1:
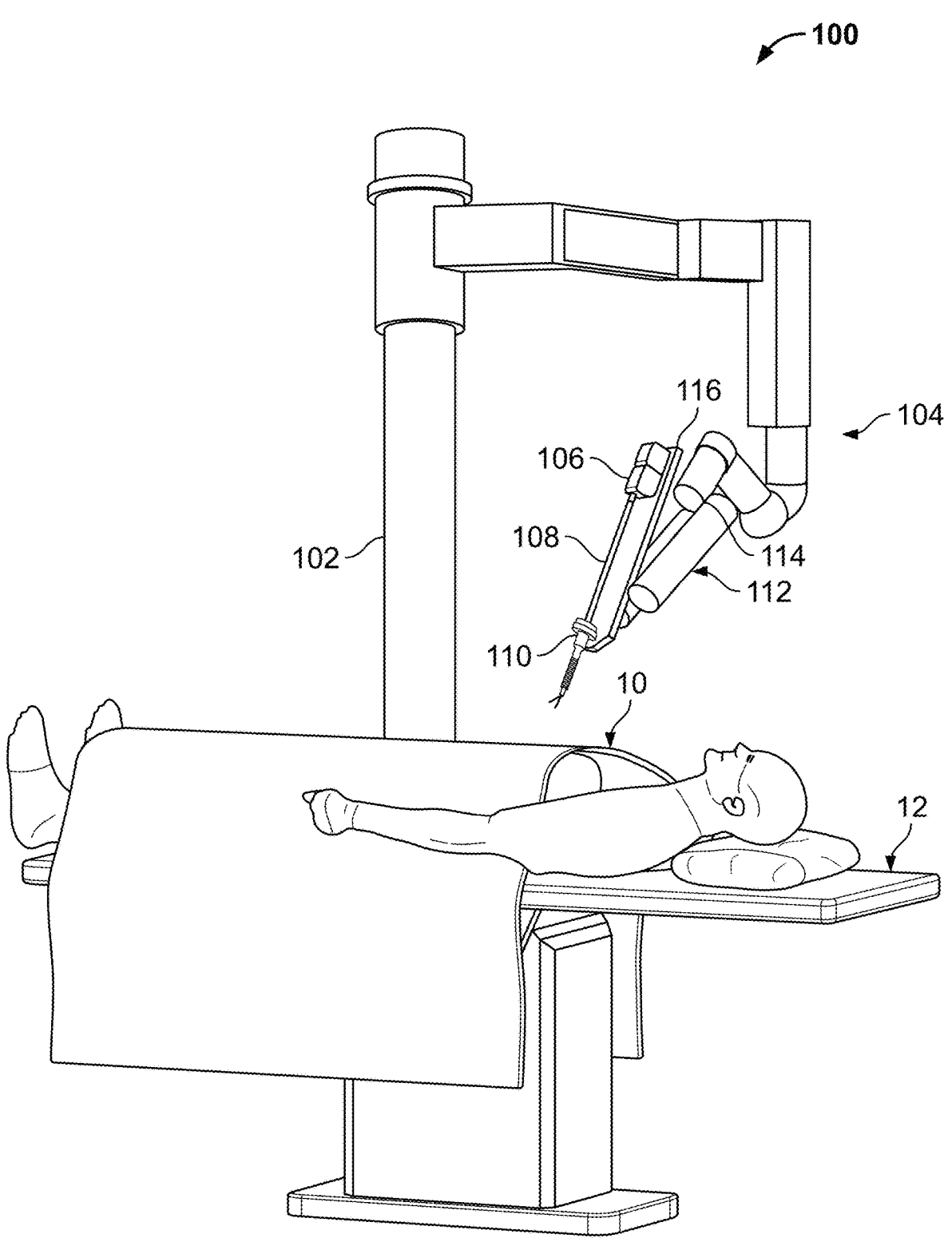
FIG. 1 is a perspective view of a portion of a teleoperated surgical system including a surgical instrument in accordance with one or more embodiments of the present disclosure.

FIG. 1 depicts a patient-side portion 100 of a teleoperated surgical system in accordance with one or more embodiments of the present invention. Patient-side portion 100 is a robotic system for performing minimally invasive surgery on a patient's body 10 positioned on an operating table 12. Patient-side portion 100 includes a column 102, a support assembly 104, and an instrument carriage 106. In this example, column 102 anchors patient-side portion 100 on a floor surface (not shown) proximate operating table 12. However, in other embodiments the patient-side portion may be mounted to a wall, to the ceiling, to the operating table supporting the patient's body, or to other operating room equipment. Support assembly 104 branches radially outward from the column 102, and instrument carriage 106 resides at a distal end of the support assembly. Instrument carriage 106 supports a detachable surgical instrument 108, and the carriage includes various actuators and control connections for controlling functionality of the instrument during a surgical procedure within the patient's body 10. In particular, the teleoperated actuators housed in instrument carriage

106 provide a number of controller motions that surgical instrument 108 translates into a corresponding variety of movements of the instrument's end effector. In particular, the surgical instrument includes a drive assembly housing an input device configured to facilitate controlled adjustment of the end effector, in response to actuation signals from the instrument carriage. The particulars of the instrument's drive assembly and its individual components are provided below with reference to FIGS. 2A-7B.

Returning to FIG. 1, an entry guide 110 (e.g., a cannula) serves as a surgical port to an orifice of the patient's body 10 that receives surgical instrument 108 to guide the instrument into the patient. Entry guide 110 may perform various other functions, such as allowing fluids and other materials to pass into or out of the body, and reducing trauma at the surgical site by isolating at least some motion of the surgical instrument (e.g., translating movement along an insertion axis, and/or axial (lengthwise) rotation of the instrument shaft around the insertion axis) from the body wall.

Support assembly 104 further includes an instrument manipulator 112 that controls positioning of surgical instrument 108 relative to the patient's body 10. In various implementations, instrument manipulator 112 may be provided in a variety of forms that allow surgical instrument 108 to move with one or more mechanical degrees of freedom (e.g., all six Cartesian degrees of freedom, five or fewer Cartesian degrees of freedom, etc.). Typically, mechanical or control constraints restrict instrument manipulator 112 to move surgical instrument 108 around a particular center of motion that stays stationary with reference to the patient's body 10. This center of motion is typically located proximate where surgical instrument 108 enters the patient's body 10 (e.g., at some point along entry guide 110, such as the midpoint of the body wall). In this example, instrument manipulator 112 includes a joint 114 and an elongated spar 116 supporting instrument carriage 106 and entry guide 110. In this example, instrument carriage 106 is mounted to ride along the length of spar 116 while entry guide 110 is held fixed, so as to translate surgical instrument 108 through the entry guide along an insertion axis relative to the patient's body 10. Adjusting joint 114 locates surgical instrument 108 at a desired angular orientation about the center of motion, while movement of carriage 106 along spar 116 locates the surgical instrument at a desired insertion point through the center of motion. Thus, the teleoperated actuators of instrument manipulator 112 move surgical instrument 108 as a whole, as compared to the teleoperated actuators housed in instrument carriage 106, which move only the instrument's end effector or other individual instrument components. Manipulator 112 is illustrative of both manipulators that are configured to constrain the remote center of motion by fixed intersecting manipulator joint axes (hardware-constrained remote center of motion) and manipulators controlled by software to keep a defined remote center of motion fixed in space (software-constrained remote center of motion).

The term "surgical instrument" is used herein to describe a medical device for insertion into a patient's body and use in performing surgical or diagnostic procedures. A surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some surgical instruments used with embodiments of the invention further provide an articulated support (sometimes referred to as a "wrist") for the end effector so that the position and orientation of the end effector can be manipulated with one or more mechanical degrees of freedom in relation to the instrument's shaft. Further, many surgical end effectors include a functional mechanical degree of freedom, such as jaws that open or close, or a knife that translates along a path. Surgical instruments appropriate for use in one or more embodiments of the present disclosure may control their end effectors (surgical tools) with one or more rods and/or flexible cables. In some examples, rods, which may be in the form of tubes, may be combined with cables to provide a pull, push, or combined "push/pull" or "pull/pull" control of the end effector, with the cables providing flexible sections as required. A typical elongate shaft for a surgical instrument is small, for example five to eight millimeters in diameter. The diminutive scale of the mechanisms in the surgical instrument creates unique mechanical conditions and issues with the construction of these mechanisms that are unlike those found in similar mechanisms constructed at a larger scale, because forces and strengths of materials do not scale at the same rate as the size of the mechanisms. The rods and cables must fit within the elongate shaft and be able to control the end effector through the wrist joint. The cables may be manufactured from a variety of metal (e.g., tungsten or stainless steel) or polymer (e.g., high molecular weight polyethylene) materials. Polymer cables may be preferred in some embodiments to enable a discrete, multi-step pretensioning process. Polymer cables may be more suitable for such processes because they are not as stiff as metal cables and tend to release unintentional over-tensioning. For example, polymer cables tend to "creep" more than the metal cables, which may enable the pre-tension on all cables to become equal (or substantially equal) over time. As will become apparent from the discussion below, this effect may be particularly beneficial because the interlocking splines employed in certain embodiments may only allow for discrete changes in cable pre-tensioning (e.g., shifting one tooth of the splines may change the cable tension by 1 lbf, but a ½ lbf adjustment may not be possible in certain configurations). This "creep" effect of polymer cables allows any cable that ends up at a higher tension than others to gradually drop to a lower pretension over time.

Figures 2A, 2B:
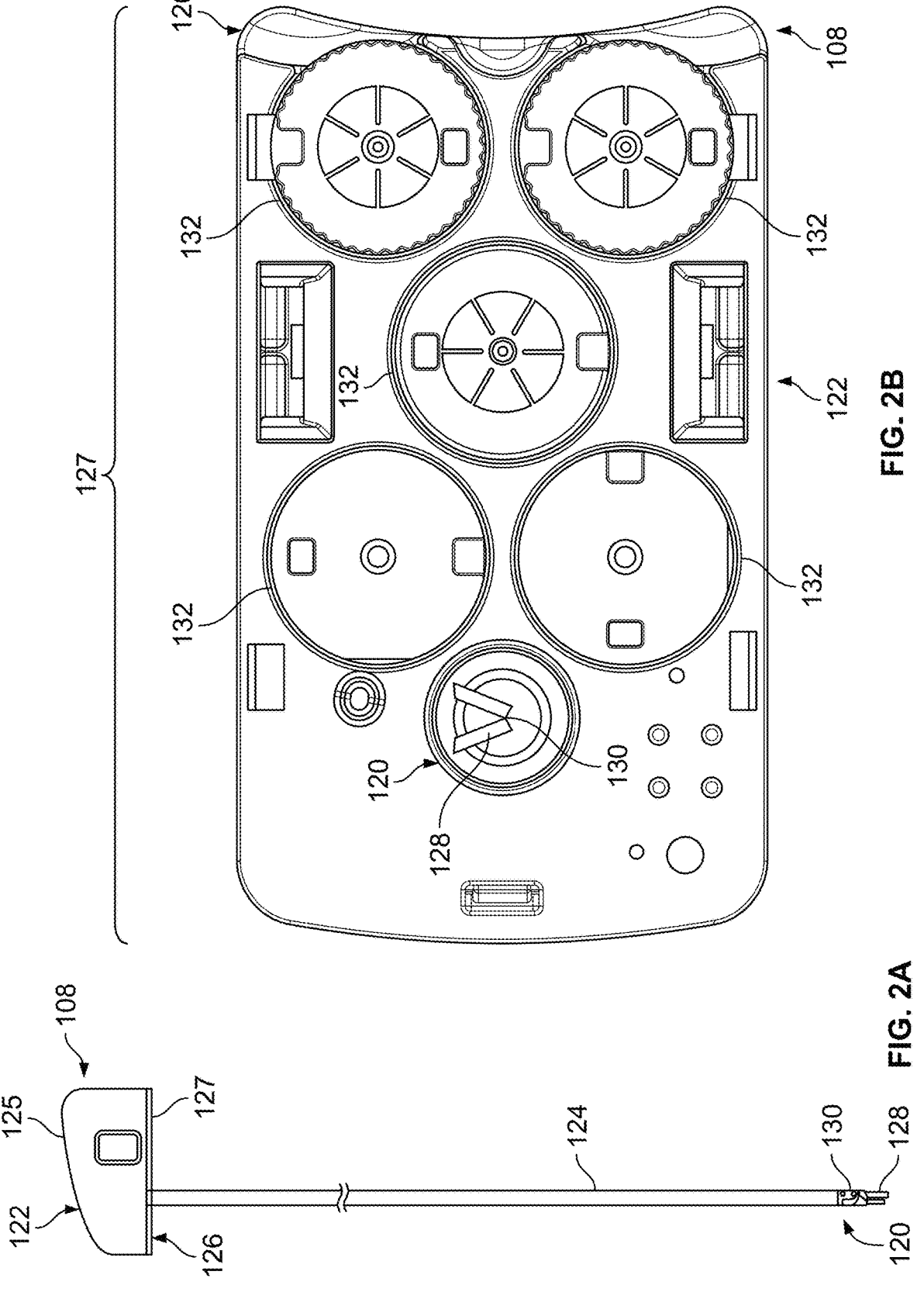
FIG. 2A is a side view of a surgical instrument including a drive assembly having an input device in accordance with one or more embodiments of the present disclosure.
FIG. 2B is a bottom view of the drive assembly of FIG. 2A.

FIG. 2A illustrates a surgical instrument 108 including a distal portion 120 and a proximal drive assembly 122 coupled to one another by an elongate shaft 124 defining an internal bore. Drive assembly 122 includes a housing 125 supporting an input device 126. Input device 126 includes an instrument control surface 127. The input device facilitates controlled adjustment of the instrument's end effector via a drive cable extending along the internal bore of the elongate instrument shaft.

Control surface 127 provides mechanical connections to the other control features of surgical instrument 108. During use, instrument control surface 127 couples to instrument carriage 106 (see FIG. 1), which controls surgical instrument 108, as generally described above. Distal portion 120 of surgical instrument 108 may provide any of a variety of surgical tools, such as the forceps 128 shown, a needle driver, a cautery device, a cutting tool, an imaging device (e.g., an endoscope or ultrasound probe), or a combined device that includes a combination of two or more various tools and imaging devices. Further, in the illustrated embodiment, forceps 128 are coupled to elongate shaft 124 by a wrist joint 130, which allows the orientation of the forceps to be manipulated with reference to the elongate shaft 124.

The bottom view of surgical instrument 108 shown in FIG. 2B illustrates control surface 127 of input device 126. As shown, control surface 127 includes a set of eight steering inputs 132, each of which governs a different aspect of movement by wrist joint 130 and forceps 128. Of course, more or less steering inputs 132 can be provided in different implementations. When control surface 127 is coupled to instrument carriage 106, each of steering inputs 132 interfaces with an actuator that drives the steering input. In this example, steering inputs 132 are configured to form a direct mechanical engagement with respective rotary actuators (e.g., servo motors) of instrument carriage 106. However, other suitable configurations for power transmission can also be used (e.g., indirect mechanical couplings including speed and/or torque converters, fluid couplings, and/or electrical couplings). Each of steering inputs 132 is part of a drive shaft (e.g., drive shaft 136 shown in FIG. 3) that operates a drive cable (e.g., drive cable 143 shown in FIG. 3) controlling movement of forceps 128.

Figure 3:
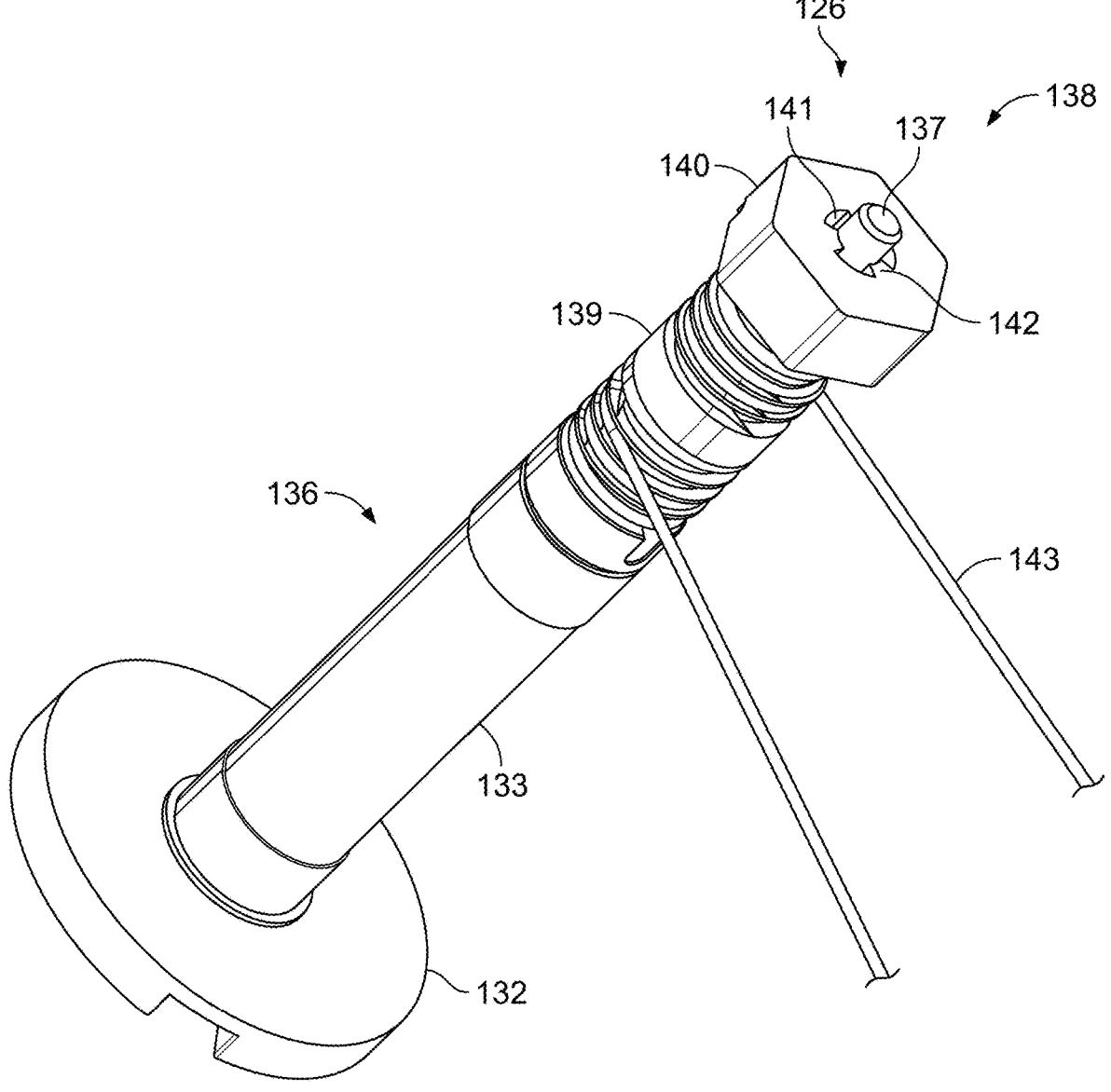
FIG. 3 is a perspective view of a portion of the input device carrying a drive cable.
Figure 4:
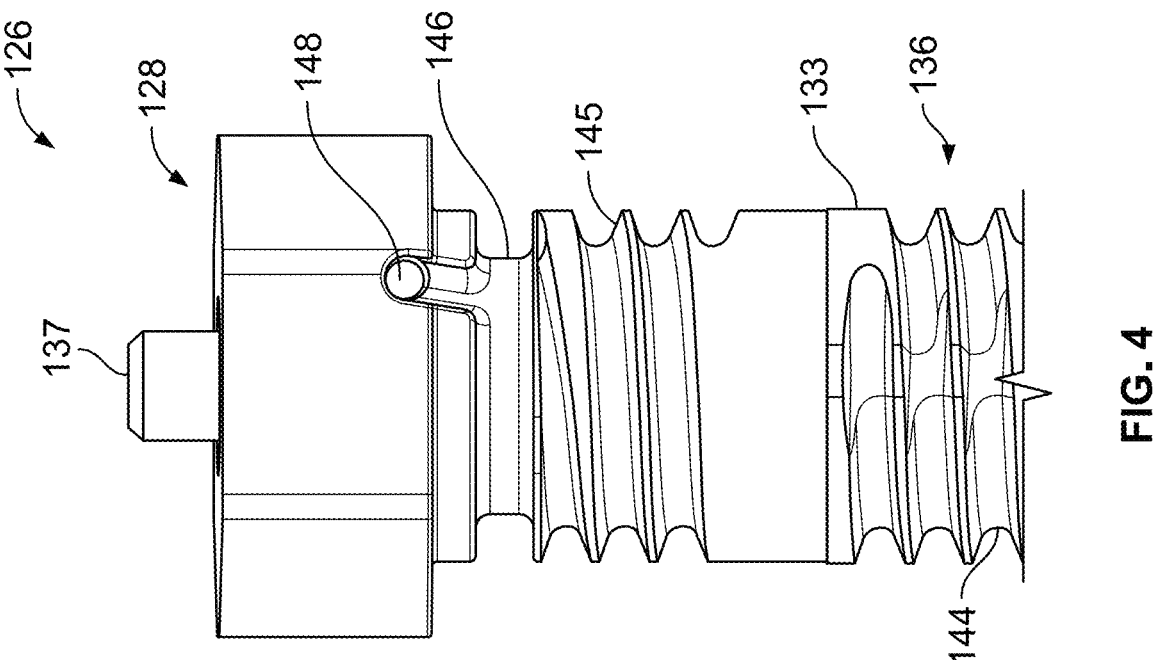
FIG. 4 is an enlarged partial side view of the input device.

FIGS. 3 and 4 illustrate an isolated portion of input device 126. The illustrated portion of input device 126 includes drive shaft 136, of which a steering input 132 is a constituent part, and a capstan 138. Drive shaft 136 and capstan 138 are separate and independent structures, illustrated here in a releasable engaged state. As discussed in detail below, while in the engaged state, relative rotation between drive shaft 136 and capstan 138 is at least inhibited (or entirely prevented, in some examples). As shown, drive shaft 136 includes the disk-shaped steering input 132 and a cylindrical rod 133 extending outward from the steering input along the steering input's axis of rotation. Drive shaft 136 further includes a support stem 137 extending from a bore of cylindrical rod 133. In this example, steering input 132 and cylindrical rod 133 are thermoplastic parts (e.g., nylon or polycarbonate) that are overmolded around the metallic support stem 137.

Capstan 138 is a contiguous and monolithic bolt-shaped structure including a tubular shank 139 and a flat-top, polygonal head 140. The head is hexagonal in this example, but other configurations are also envisioned. A central bore 141 extends longitudinally through both shank 139 and head 140. Inwardly projecting prongs 142 located in the region of head 140 extend from the wall of bore 141 towards the center of capstan 138 to surround support stem 137 of drive shaft 136 (see FIG. 3). When drive shaft 136 and capstan 138 are disengaged and independently rotatable relative to one another, support stem 137 functions as a spindle that provides a central axis of rotation for the capstan. Additional features of drive shaft 136 and capstan 138 are discussed below with reference to FIGS. 5-7B.

With continued reference to FIG. 3, input device 126 carries a drive cable 143. One end of drive cable 143 is attached to drive shaft 136, and an opposite end of drive cable 143 is attached to capstan 138. The respective ends of drive cable 143 are fixed to drive shaft 136 and capstan 138 by friction couplings. In this example, the ends of drive cable 143 are tightly wound around the respective components of input device 126 for multiple revolutions to provide sufficient surface friction to maintain the couplings intact. Both drive shaft 136 and capstan 138 include outwardly facing helical grooves 144,145 to guide the winding of the cable ends (see FIG. 4). Capstan 138 further includes an outwardly facing spool 146 and a tortuous path 148 (see FIG. 4). Spool 146 is provided in the form of a channel of significantly larger width than that of helical grooves 144, so as to support multiple overlapping cable windings. Tortuous path 148 extends through capstan 138 in a direction at or near a right angle (e.g., perpendicular) to its longitudinal axis. Tortuous path 148 includes two or more sharp bends traversable by drive cable 143 to further enhance the surface friction with capstan 138. During assembly, drive cable 143 is first guided through tortuous path 148, and then wrapped over itself several times in spool 146 before being routed into helical grooves 144. Drive cable 143 partially wraps and releases itself from helical grooves 144 as capstan 138 rotates, but the windings secured in spool 146 remain fixed in place. The spool and tortuous path are features that facilitate a purely frictional coupling between the drive cable and capstan. This purely frictional coupling enables the use of cables without added end attachments (e.g., crimps), which further simplifies manufacturing and installation processes. Such features enable the use of polymer cables, which, as noted above, may be preferred in some implementations. Although purely frictional couplings may be advantageous at times, the present disclosure fully contemplates the use of crimps, fittings, other types of mechanical fasteners, and similar techniques (e.g., welding, fusing, over-molding, etc.) suitable for coupling the drive cable to the capstan. Moreover, while not presently shown and described in detail, drive shaft 136 may also be provided with substantially similar features as capstan 138 to facilitate a secure coupling with drive cable 143.

Though only a short section is shown, the middle portion of drive cable 143 between the ends carried by input device 126 extends into the internal bore of the surgical instrument's elongate shaft 124. As described above, drive cable 143 traverses the internal bore and couples to an end effector of the surgical instrument. Power provided by an actuator of the instrument carriage is transmitted to drive shaft 136 via steering input 132, causing the drive shaft to rotate. With the components of input device 126 in the engaged state, the rotary motion of drive shaft 136 is directly transferred to capstan 138. Shared rotation of drive shaft 136 and capstan 138 causes the respective ends of drive cable 143 to equally release from or further entwine these components. As shown in FIG. 3, the cable ends are wound about the drive shaft and capstan in opposite directions, such that their simultaneous rotation in a clockwise direction causes one end of the cable to release from the capstan while the other end becomes further wound about the drive shaft, and vice versa with counter-clockwise rotation. Such controlled movement of drive cable 143 facilitates operation of the "push/pull" or "pull/pull" mechanism for working the end effector.

Figure 5:
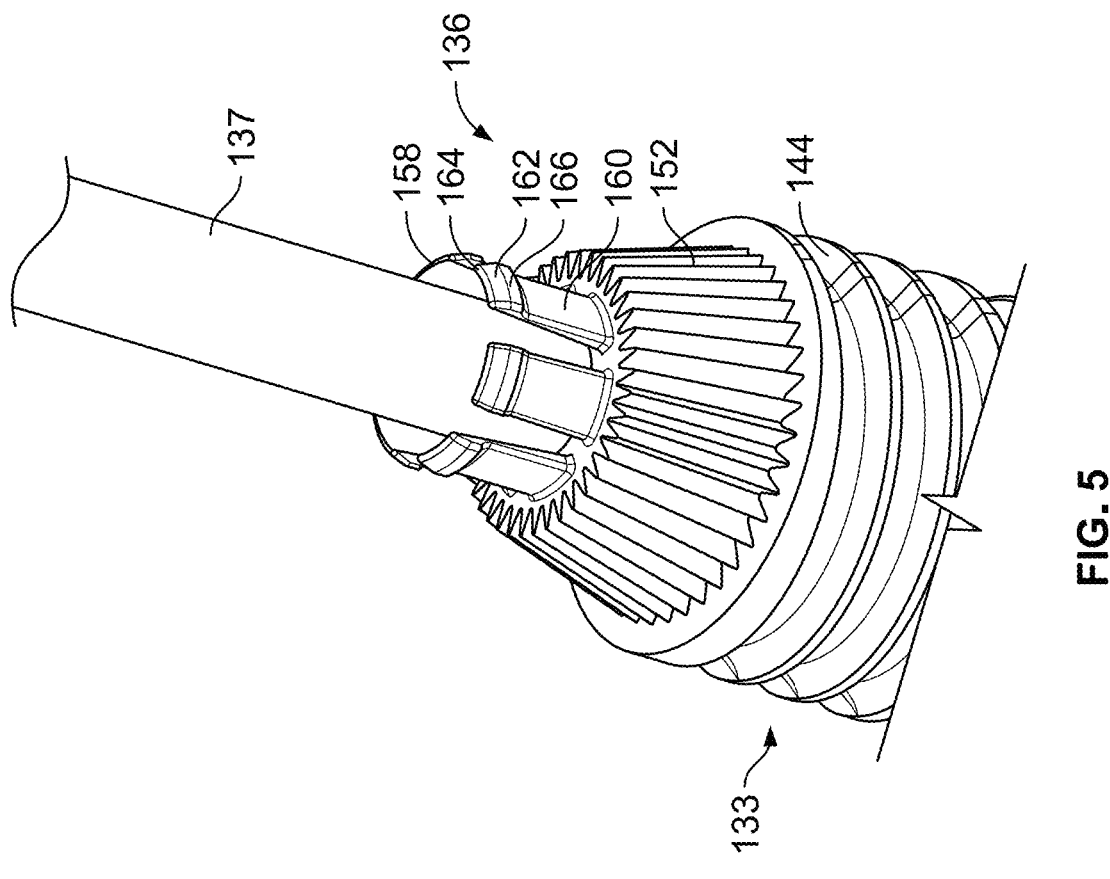
FIG. 5 is a perspective view of a drive shaft of the input device.
Figures 6A, 6B:
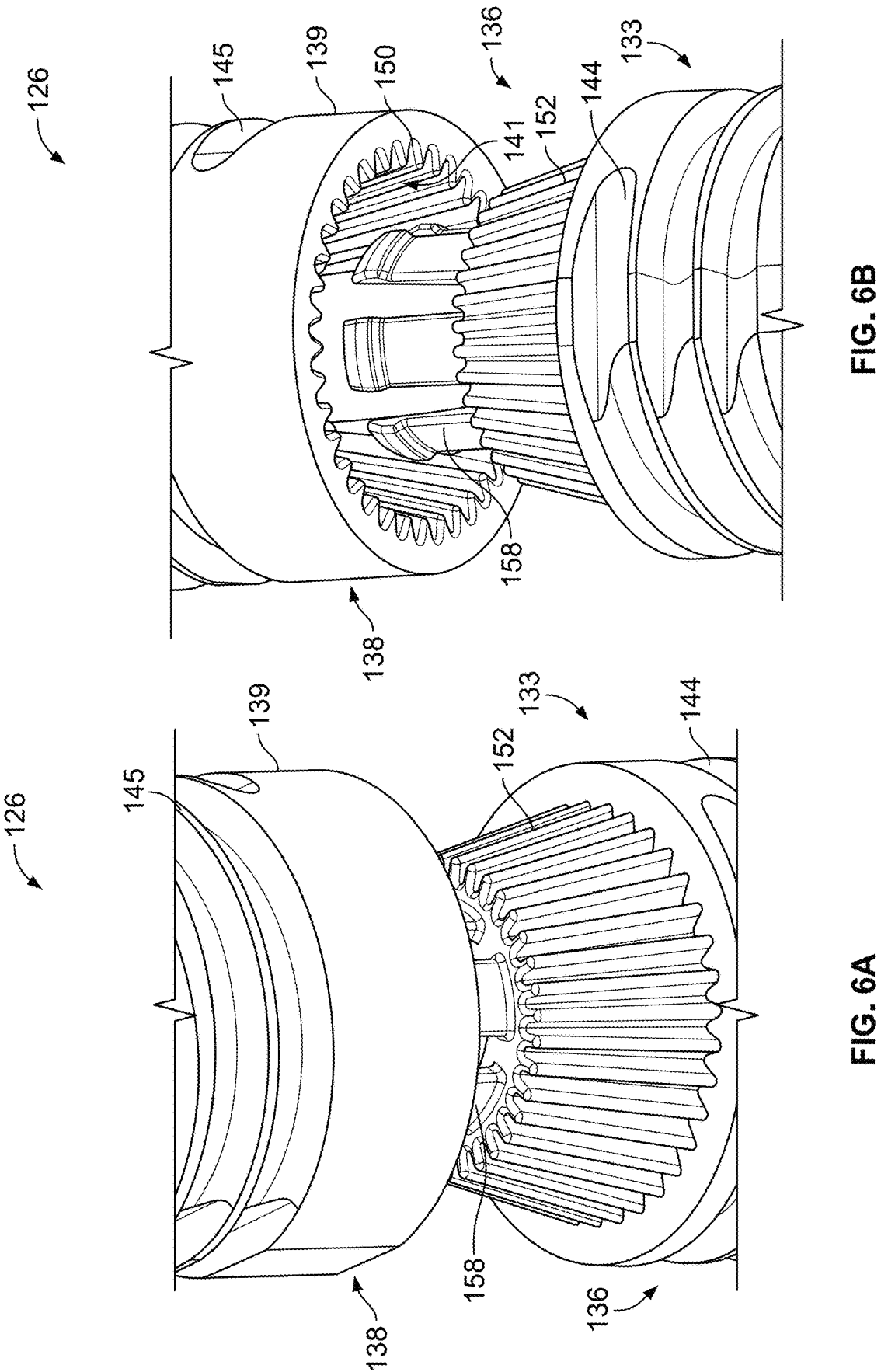
FIGS. 6A and 6B are perspective top and bottom views of the input device illustrating a capstan being lowered into the drive shaft.

Turning next to FIGS. 5, 6A, and 6B, engagement of drive shaft 136 and capstan 138 is enabled by a plurality of diametrically spaced vertical splines 150 (see FIG. 6B). Splines 150 are located in the region of shank 139, projecting inwardly from the wall of the capstan's central bore 141 (see FIG. 6B). As shown, splines 150 are radially tapered along the longitudinal direction of capstan 138, such that the degree of inward protrusion decreases along the length of the capstan in a downward direction (i.e., the longitudinal direction leading from head 140 to shank 139). Thus, the plurality of vertical splines 150 forms the lower shank portion of capstan bore 141 into a reverse-frustoconical cavity. In this example, cylindrical rod 133 of drive shaft 136 also includes a plurality of vertical splines 152. Splines 152 are diametrically spaced along an outer surface of cylindrical rod 133, located just above helical grooves 144. The splines of the drive shaft are specifically designed to engage the splines of the capstan. Thus, splines 152 are also radially tapered, but in the opposite (i.e., upward) direction. The plurality of splines 152 form a frustoconical structure on drive shaft 136 that is appropriately sized to be accommodated by the reverse-frustoconical cavity of the capstan's central bore 141. When capstan 138 is fitted over and pressed down upon drive shaft 136, splines 150 and 152 form a keyed interlocking mesh preventing relative movement therebetween. The conical nature of the respective splines serves to ease the meshing action between them, and it may also reduce wear in certain configurations and conditions. Further, as shown particularly well in FIGS. 6A and 6B, splines 150 and 152 are provided with relatively smooth chamfered edges at their ends. These chamfered end edges serve a dual purpose of inhibiting stress concentrations and also providing lead-in surfaces angled from the vertical direction of the splines 150,152 that facilitate meshing. The lead-in function of the chamfered edges allows the splines to self-correct slight misalignments by sliding past one another into engagement under a slight downward force. This self-correction feature of the mating splines is one of several features that simplify assembly, enabling automation.

Drive shaft 136 further includes a plurality of diametrically spaced snap fingers 158 located atop splines 152. The snap fingers are provided to effectively lock the capstan onto the drive shaft in the vertical direction to inhibit unintentional disengagement during use. As noted below, while the snap fingers may securely hold the capstan in place on the drive shaft, they may also permit its release in response to sufficient upward force. The snap fingers provide a quick coupling operable without special tools or additional fasteners that prohibits unintentional release of the capstan while also permitting its intentional release. Thus, the snap fingers are yet another feature of the input device that provides a simplified assembly process.

In this example, each of snap fingers 158 includes an elastic stem 160 and a lip 162 projecting radially outward from an upper end of the stem to engage an undercut ridge (not shown) along bore 141 of capstan 138. When the protruding lips of the fingers meet the ridge under a downward external force, the elastic stems are pressed inward until the lips snap passed the ridge, allowing the stems to recover to their initial position. The protruding lips then bear against the ridge to resist vertical movement between the drive shaft and capstan. Each of lips 162 features both upper and lower beveled edges 164,166. Upper beveled edge 164 facilitates sliding contact with the undercut ridge as capstan 138 is pushed downward relative to drive shaft 136 to place the component in an engaged state. Lower beveled edge 166 facilitates sliding contact with the ridge as capstan 138 is pulled upward relative to drive shaft 136 to release the components from the engaged state.

In other examples, a snap finger lip engages a groove in the capstan bore. The elastic stems are biased outwards so that each lip snaps into the groove on engagement. The lips are optionally beveled to facilitate insertion into the capstan bore and disengagement from the groove.

As noted above, drive shaft 136 and capstan 138 are separate and independent structures capable of transitioning between an "engaged" state (see FIG. 7B), where relative rotation between them is inhibited, and a released or "disengaged" state (see FIG. 7A), where relative rotation between them is freely permitted. Drive shaft 136 and capstan 138 are placed in the engaged state prior to use in order to facilitate push/pull or pull/pull operation of the end effector via drive cable(s) 143, as described above. These components are placed in the disengaged state to facilitate tuning or "pre-tensioning" of drive cable 143. Pre-tensioning drive cable 143 is a necessary step in assembly and configuring surgical instrument 108, so that the end effector (e.g., forceps 128) is accurately and rapidly responsive to rotation of drive shaft 136 and capstan 138.

Figures 7A, 7B:
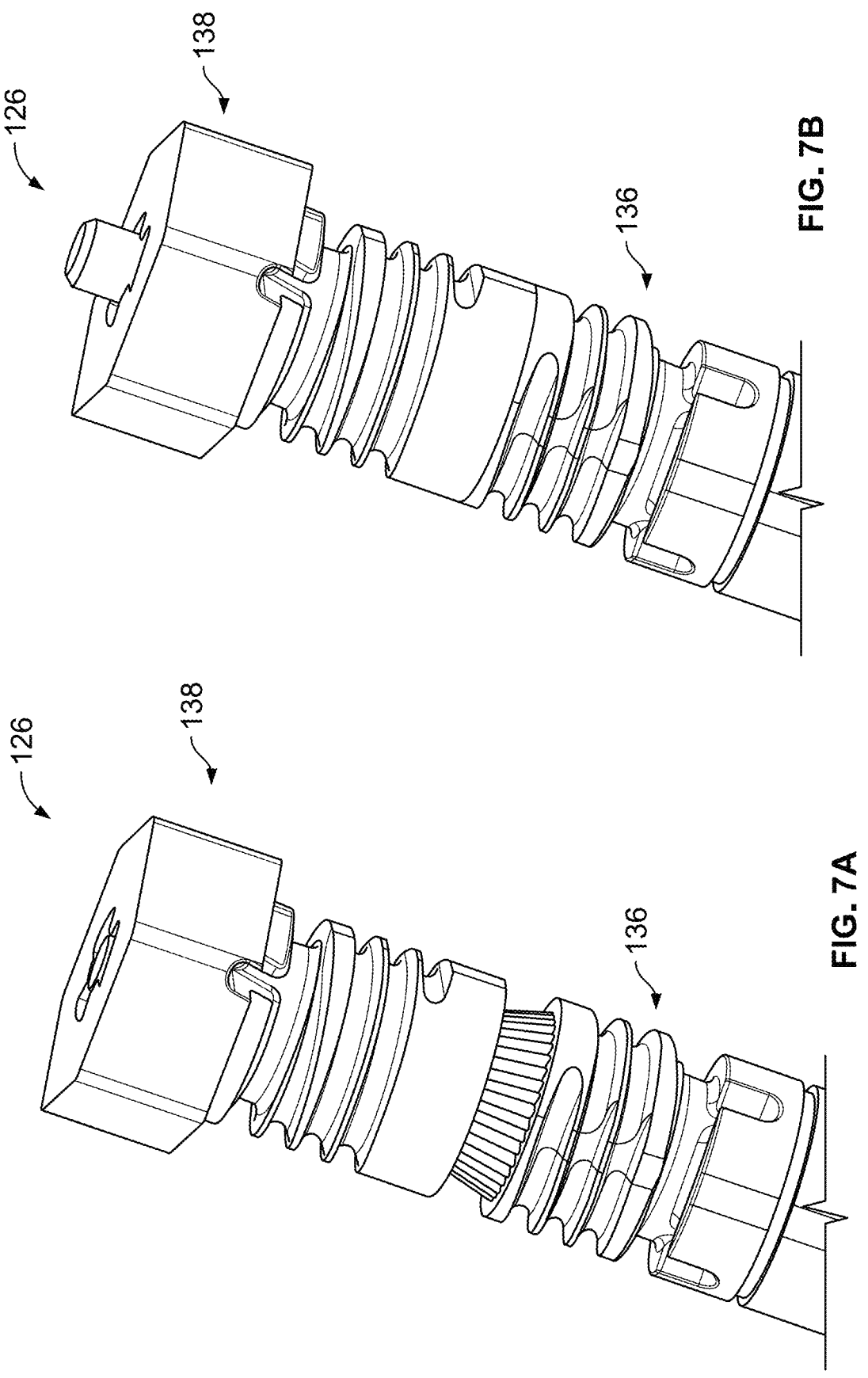
FIGS. 7A and 7B are perspective views of the input device illustrating the capstan and drive shaft in respective disengaged and engaged states.
Figure 8:
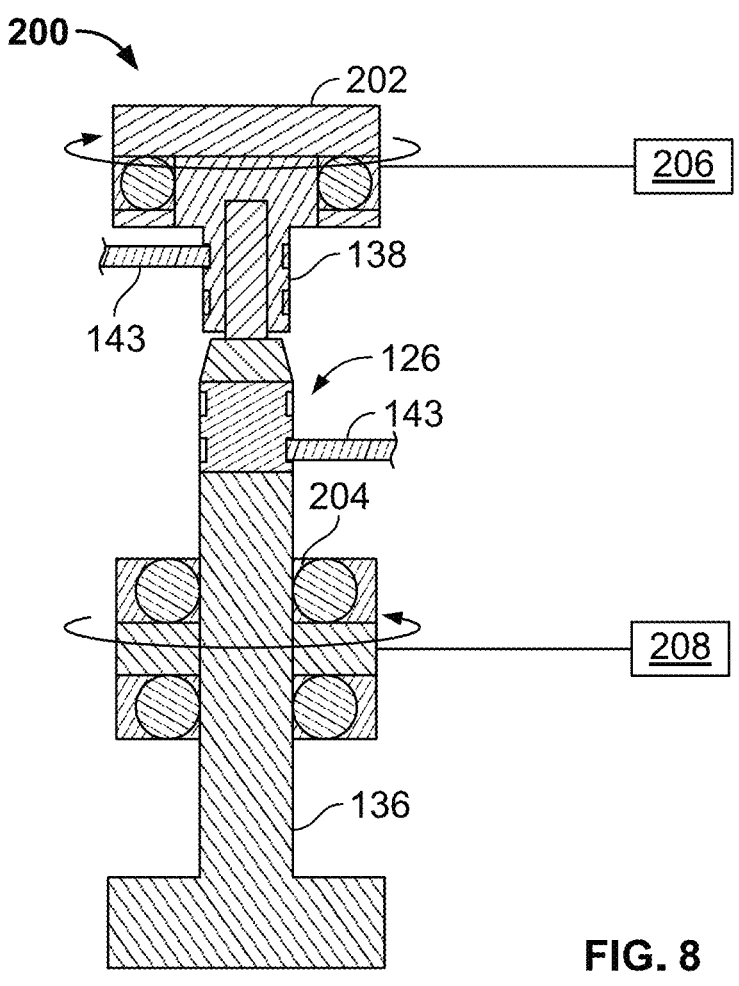
FIG. 8 is a functional diagram of the input device illustrating a method for tensioning the drive cable.

Referring next to FIGS. 8A and 8B, pre-tensioning of drive cable 143 can be performed using an apparatus 200 appropriately configured to independently rotate drive shaft 136 and capstan 138 when these components in the disengaged state (see FIG. 7B). In this example, apparatus 200 includes a first drive mechanism 202 and a second drive mechanism 204. First drive mechanism 202 is powered by a first motor 206, and second drive mechanism 204 is powered by a second motor 208. As shown, drive shaft 136 is carried by first drive mechanism 202, and capstan 138 is carried by second drive mechanism 204. As discussed below, the two drive mechanism can be used to pre-tension the drive cable by rotating the drive shaft and capstan alternatively or simultaneously.

Figure 9:
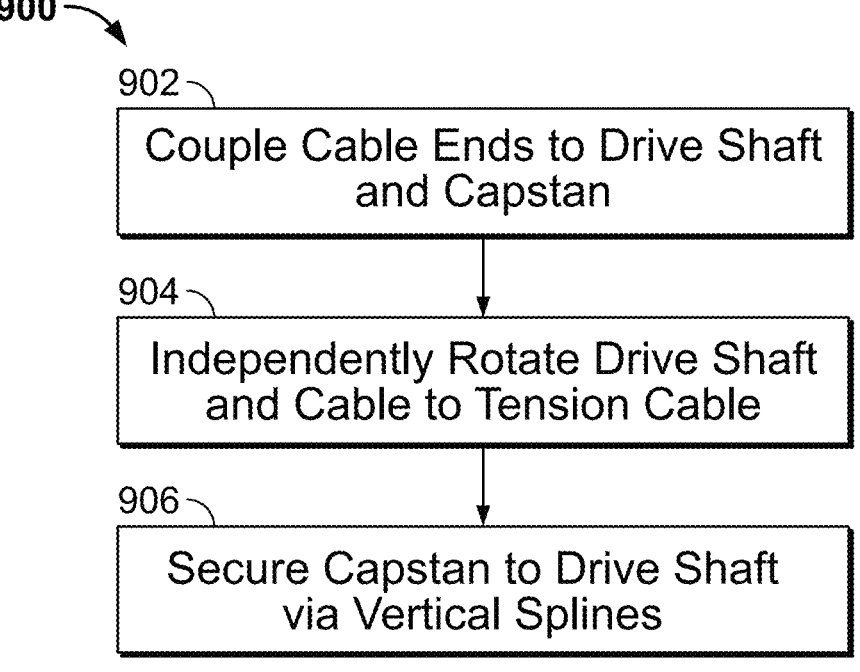
FIG. 9 is a flow chart illustrating a method of tensioning a cable of a drive assembly for a surgical instrument.

FIG. 9 illustrates a method 900 of tensioning a cable of a drive assembly for a surgical instrument. For purposes of clarity, the method 900 will be described in the context of apparatus 200 and input device 126, the individual components of which are described above. Step 902 of method 900 includes coupling the respective ends of drive cable 143 to drive shaft 136 and capstan 138. In some examples, the ends of the cable of attached to the drive shaft and capstan by purely frictional couplings, absent additional connection hardware (e.g., crimps or other fasteners). For instance, the cable ends may be wound around the drive shaft and capstan. In some examples, coupling an end of the cable to the drive shaft or capstan includes routing the cable through two or more sharp bends of a tortuous path, winding the cable around a spool, and then routing the cable along an outwardly facing helical groove.

Step 904 of method 900 includes independently rotating drive shaft 136 and capstan 138 to draw cable 143 into tension. As discussed above, such independent rotation can be performed when the capstan is placed over the drive shaft, rotationally supported by the shaft's support stem, and the components are in the disengaged state, with the respective splines unmeshed. Independent rotation of the drive shaft 136 and capstan 138 may be performed by separately powering first and second drive mechanisms 202,204 via first and second motors 206,208. In some examples, the drive shaft and capstan can be rotated alternatively, with one of the components being held fixed while the other is driven. In some other examples, the drive shaft and capstan can be rotated simultaneously.

Step 906 of method 900 includes securing capstan 138 to drive shaft 136 by engaging a plurality of vertical splines of the capstan with an outer surface of the drive shaft, such that relative rotation between the drive shaft and the capstan is inhibited by the engaged splines. In some examples, engaging the plurality of vertical splines of the capstan includes meshing the splines with a mating set of vertical splines of the drive shaft. As discussed above, the splines of the capstan are on an internal bore in the capstan, and the splines of drive shaft are on an outer surface. In some examples, the respective splines are radially tapered, providing complementary frustoconical shapes. In some examples, securing the capstan to the drive shaft further includes engaging a plurality of snap fingers of the drive shaft with an undercut ridge formed along an internal bore of the capstan, such that relative vertical movement between the drive shaft and the capstan is resisted. Thus, the capstan can be secured to the driveshaft to place the components in an engaged state by simply pressing the capstan down over the drive shaft to simultaneously engage the splines and the snap fingers. As noted above, the snap fingers may be designed to permit the release of the capstan from engagement with the drive shaft. As such, further tensioning can be performed by releasing the capstan, again independently rotating the capstan and drive shaft, and then re-engaging the capstan.

The use of terminology such as "top," "bottom," "over," "upward," "downward," "upper," "lower," etc. throughout the specification and claims is for describing the relative positions of various components of the system and other elements described herein. Similarly, the use of any horizontal or vertical terms to describe elements is for describing relative orientations of the various components of the system and other elements described herein. Unless otherwise stated explicitly, the use of such terminology does not imply a particular position or orientation of the system or any other components relative to the direction of the Earth gravitational force, or the Earth ground surface, or other particular position or orientation that the system other elements may be placed in during operation, manufacturing, and transportation.

A number of embodiments of the invention have been described. Nevertheless, it will be understood that various modifications may be made without departing from the spirit and scope of the inventions. For example, in some embodiments, only one of the capstan or the drive shaft includes radial splines, and these splines engage an unsplined surface of the mating capstan/drive shaft component. In other embodiments the features described on the drive shaft (e.g., tapered projection, splines on the projection, snap fit element) may be placed on the capstan, and the features described on the capstan (e.g., tapered bore, splines on the bore, engagement for snap-fit element) may be placed on the drive shaft. Further, embodiments of assembly methods may be reversed for disassembly. In addition, it should be understood that various described components and features optionally may be combined, so that one or more features of one embodiment may be combined with, or substituted for, one or more features of another embodiment consistent with the inventive aspects.

What is claimed is:

1. A method for assembling a drive assembly for transmitting actuation force to a surgical instrument end effector coupled to an instrument shaft via cable tensioning, the method comprising:

coupling, to a drive shaft of the drive assembly, a first cable portion of a drive cable, the drive cable extending along the instrument shaft and operably coupled to the end effector, coupling, to a capstan of the drive assembly, a second cable portion of the drive cable, independently rotating the drive shaft relative to the capstan to draw the drive cable into tension, and securing the capstan and the drive shaft in a fixed rotational relationship with each other via a splined snap-fit connection mechanism.

2. The method of claim 1, wherein the coupling of the first cable portion and the coupling of the second cable portion occur in a state when the drive shaft and the capstan are disengaged from each other.

3. The method of claim 1, wherein the independent rotation of the drive shaft relative to the capstan to draw the drive cable into tension is performed by rotating the drive shaft only.

4. The method of claim 1, wherein the independent rotation of the drive shaft relative to the capstan to draw the drive cable into tension is performed by rotating the capstan only.

5. The method of claim 1, wherein the independent rotation of the drive shaft relative to the capstan to draw the drive cable into tension is performed by rotating the capstan and the drive shaft.

6. The method of claim 5, wherein the independent rotation of the drive shaft relative to the capstan occurs by using a first motor and a second motor to respectively independently rotate each of the drive shaft and the capstan.

7. The method of claim 5, wherein the independent rotation of the drive shaft relative to the capstan comprises alternatively rotating the drive shaft and the capstan, with one of the drive shaft and the capstan being held fixed, while the other one of the drive shaft and the capstan is driven.

8. The method of claim 5, wherein the independent rotation of the drive shaft relative to the capstan comprises rotating the drive shaft and the capstan simultaneously.

9. The method of claim 1, wherein coupling the first cable portion of the drive cable to the drive shaft or the second cable portion of the drive cable to the capstan includes:

routing the drive cable through a plurality of bends of a tortuous path of the capstan, winding the drive cable around a spool of the capstan, and routing the drive cable along an outwardly facing helical groove.

10. The method of claim 1, wherein the securing the drive shaft and the capstan in a fixed rotational relationship with each other comprises using splined engagement features of the splined snap-fit connection mechanism.

11. The method of claim 1, further comprising securing the drive shaft and the capstan in a fixed axial relationship using snap-fit engagement features of the splined snap-fit connection mechanism.

12. The method of claim 1, wherein the drive cable is made of a polymer material.

13. A surgical instrument, comprising:

an instrument shaft;

an end effector coupled to the instrument shaft; and a drive assembly coupled to the instrument shaft, the drive assembly comprising:

a drive cable extending along the instrument shaft and operably coupled to the end effector, a drive shaft receiving a first portion of the drive cable; and a capstan receiving a second portion of the drive cable, wherein the capstan and the drive shaft are transitionable between an engaged state with each other and a disengaged state with each other, and wherein, in the engaged state, the capstan and the drive shaft are secured in a fixed rotational relationship with each other via a splined snap-fit connection mechanism.

14. The surgical instrument of claim 13, wherein the drive shaft and the capstan are secured in the fixed rotational relationship with each other by using splined engagement features of the splined snap-fit connection mechanism.

15. The surgical instrument of claim 14, wherein the splined engagement features of the splined snap-fit connection mechanism comprise a first plurality of splines projecting from a wall of a central bore of the capstan.

16. The surgical instrument of claim 15, wherein the splined engagement features of the splined snap-fit connection mechanism further comprise a second plurality of splines included in a cylindrical rod of the drive shaft.

17. The surgical instrument of claim 16, wherein the first plurality of splines are radially tapered along a longitudinal direction of the capstan.

18. The surgical instrument of claim 17, wherein the second plurality of splines are radially tapered in a direction opposite to the first plurality of splines.

19. The surgical instrument of claim 13, wherein, in the engaged state, the capstan and the drive shaft are secured in a fixed axial relationship using snap-fit engagement features of the splined snap-fit connection mechanism.

20. The surgical instrument of claim 13, wherein, in the disengaged state:

the drive shaft is coupled to a first cable portion of the drive cable, the capstan is coupled to a second cable portion of the drive cable, and the drive shaft is independently rotated relative to the capstan to draw the drive cable into tension.

* * * * *